(12) United States Patent
Zanon et al.

(10) Patent No.: US 8,378,106 B2
(45) Date of Patent: Feb. 19, 2013

(54) METHOD FOR PREPARING ARGATROBAN MONOHYDRATE AND A PROCESS FOR ITS SYNTHESIS

(75) Inventors: Jacopo Zanon, Venice (IT); Giovanna Libralon, Galliera Veneta (IT); Andrea Nicole', Ponte S. Nicolo' (IT)

(73) Assignee: Lundbeck Pharmaceuticals Italy S.p.A., Padua (IT)

( * ) Notice: Subject to any disclaimer, the term of this patent is extended or adjusted under 35 U.S.C. 154(b) by 229 days.

(21) Appl. No.: 12/935,512

(22) PCT Filed: Apr. 6, 2009

(86) PCT No.: PCT/EP2009/054085
§ 371 (c)(1),
(2), (4) Date: Sep. 29, 2010

(87) PCT Pub. No.: WO2009/124906
PCT Pub. Date: Oct. 15, 2009

(65) Prior Publication Data
US 2011/0028726 A1    Feb. 3, 2011

(30) Foreign Application Priority Data
Apr. 7, 2008   (IT) .............................. PD2008A0106

(51) Int. Cl.
*C07D 215/38* (2006.01)
(52) U.S. Cl. ...................................................... 546/159
(58) Field of Classification Search ................... 546/159
See application file for complete search history.

(56) References Cited

U.S. PATENT DOCUMENTS
4,201,863 A   5/1980 Okamoto et al. ............. 546/166

FOREIGN PATENT DOCUMENTS
EP    0 823 430    2/1998

OTHER PUBLICATIONS

Jang, Circulation Research, vol. 67(6), pp. 1552-1561, 1990.*
International Search Report and Written Opinion for corresponding PCT Application No. PCT/EP2009/054085 dated Jul. 15, 2009.
Okamoto, et al., *Potent Inhibition of Thrombin by the newly Synthesized Arginine Derivative No. 805. The Importance of Stereo-structure of it's HydrophobicCarboxamide Portion.*, Biochemical and Biophysical Research Communications, Academic Press Inc., Orlando, FL, vol. 101, No. 2, Jul. 30, 1981 (pp. 440-446).
Song, *Method for Preparing Argatroban Monohydrate in Pure Water*, Casreact, Apr. 25, 2007 (6 pages).

* cited by examiner

*Primary Examiner* — D M Seaman
(74) *Attorney, Agent, or Firm* — Ohlandt, Greeley, Ruggiero and Perle, L.L.P.

(57) ABSTRACT

A method is described for preparing argatroban monohydrate obtained from (2R,4R)-1-[$N^G$-nitro-$N^2$-(3-methyl-8-quinolinesulphonyl)-L-arginyl]-4-methyl-2-piperidine carboxylic acid by suitably treating crude argatroban. The method either comprises preparation of argatroban monohydrate in a continuous step or an intermediate step of isolating a purified argatroban. Also obtainable from argatroban monohydrate is anhydrous argatroban, shown to have new physico-chemical characteristics.

The described argatroban synthesis and purification process hence enables three different forms of argatroban, not previously described, to be obtained, each with distinctive physico-chemical characteristics and in particular enables argatroban monohydrate to be obtained with high yield and with high purity, being therefore a product suitable for use as active principle in proprietary medicines.

11 Claims, 15 Drawing Sheets

METHOD FOR PREPARING ARGATROBAN MONOHYDRATE AND A PROCESS FOR ITS SYNTHESIS

FIELD OF THE INVENTION

The present invention relates to a method for preparing argatroban monohydrate. Said method enables argatroban to be obtained in three different crystalline forms i.e. in the form of argatroban monohydrate, purified argatroban and argatroban anhydrous, each having specific and new physicochemical characteristics. The present invention also relates to the three different isolated forms, namely argatroban monohydrate, purified argatroban and argatroban anhydrous.

STATE OF THE ART

U.S. Pat. No. 4,201,863 (6 May 1980) and EP 8746 (filed on 22 Aug. 1979 with priority based on the application for the cited US patent) describe a class of $N^2$-arylsulphonyl-L-argininamide drugs, with anti-thrombotic activity, and the processes for obtaining them. Of these, the compound 4-methyl-1-[$N^2$-(3-methyl-1,2,3,4-tetrahydro-8-quinolinesulphonyl)-L-arginyl]-2-piperidine carboxylic acid (argatroban, isomers mixture) is described. The described process comprises the synthesis of an intermediate $N^G$-substituted-$N^2$-quinolinesulphonyl-L-argininamide from which the desired compound is obtained by catalyzed hydrogenolysis or acidolysis and catalyzed hydrogenation. The general conditions provided for the hydrogenolysis and hydrogenation reaction are: i) inert solvents (methanol, ethanol, tetrahydrofuran or dioxane); ii) presence of a catalyst (Raney nickel, palladium, platinum, ruthenium, rhodium); iii) hydrogen atmosphere at a pressure between 1 and 100 kg/cm$^2$ and preferably between 5 and 50 kg/cm$^2$; iv) temperature between 0° C. and 200° C. and preferably between 50° C. and 150° C.; v) reaction temperature from 2 hours to 120 hours. The crude product obtained is then purified by trituration or by re-crystallization from diethyl ether-tetrahydrofuran, diethyl ether-methanol or from water-methanol or by chromatography. No example is given of this purification step. In particular, both U.S. Pat. No. 4,210,863 and EP 8746 in example 1(E) describe the preparation of argatroban, isomers mixture. This compound is obtained in amorphous form by hydrogenation of [$N^G$-nitro-$N^2$-(3-methyl-8-quinolinesulphonyl)-L-arginyl]-4-methyl-2-piperidine carboxylic acid in ethanol in the presence of Pd/C with hydrogen pressure of 10 kg/cm$^2$ at 100° C. for 8 hours. The catalyst is removed by filtration of the ethanol solution which is then evaporated without further purification and/or re-crystallization steps. In the US patent at issue as indeed in patent application EP 8746, no mention is made of polymorphic forms of the compounds and, for the obtained compound, the following characteristics are reported: Amorphous solid, I.R. (KBr) (cm$^{-1}$) 3400; 1620; 1460; 1380; Molecular composition (%): theoretical C 54.31; H 7.13; N 16.52; found (%) C 54.01; H 6.98; N 16.61.

U.S. Pat. No. 4,258,192 (24 Mar. 1981) (continuation-in-part of the aforesaid patent application U.S. Pat. No. 4,201,863) and the same patent application EP 8746 describe the stereoisomers and the preparation thereof, including argatroban used as an active principle in medicaments, i.e. the stereoisomer (2R,4R)-4methyl-[4$N^2$-(3-methyl-1,2,3,4-tetrahydro-8-quinolinesulphonyl)-L-arginyl]-2-piperidine carboxylic acid, with the following characteristics: melting point (m.p.). 188-191° C.; I.R. (KBr) (cm$^{-1}$) 3400, 1620, 1460, 1380; Molecular composition (%): theoretical C 54.31; H 7.13; N 16.52; found (%) C 54.05; H 6.94; N 16.65. The compound is prepared according to the description given in examples 1(E) in U.S. Pat. No. 4,258,192 and 2(E) and 3 in EP 8746 respectively by hydrogenation of (2R,4R) 1-[$N^G$-nitro-$N^2$-(3-methyl-1,2,3,4-tetrahydro-8-quinolinesulphonyl)-L-arginyl]-2-piperidine carboxylic acid in ethanol in presence of acetic acid catalyzed by Pd/C. After filtering the mass to remove the catalyst, the solvent is evaporated and the residue suspended in chloroform, the solution treated with a saturated sodium bicarbonate solution or 1N sodium hydroxide solution and after washing, the solvent is evaporated. The compound is then re-crystallized from ethanol. Again in this case, no reference is made to the obtainment of monohydrate polymorphic forms.

Said polymorphic forms are described instead in the publication Biochem. Biophys. Res. Comm. 1981, 101, 440-446 in the context of stereoisomer preparation. The monohydrate polymorph of the (2R,4R) stereoisomer is prepared by re-crystallization from ethanol/water and the reported characteristics are: m.p. 176-180° C.; $[\alpha]_D^{27}$ +76.1° (c 1, 0.2N HCl).

U.S. Pat. No. 5,925,760 (20 Jul. 1999) and EP 0823430 (filed 4 Aug. 1997) subsequently describe a new method for preparing argatroban by means of a new intermediate $N^2$-(3-methyl-8-quinolinesulphonyl)-$N^G$-nitro-L-arginine. In particular the patent makes reference to the preparation of a crystalline monohydrate form of argatroban, referring back to examples (D) and (E) of Japanese patent publication No. (Hei)-2-31055/1990 and generically to an I.R. spectrum identical to that of the commercially available argatroban compound. The relevant example in the cited patent publication is example (E), while example (D) concerns the preparation of (2R,4R)-1-[$N^G$-nitro-$N^2$-(3-methyl-8-quinolinesulphonyl)-L-arginyl]-4-methyl-2-piperidine carboxylic acid. This compound represents the starting compound for argatroban preparation by catalytic reduction in the presence of Pd/C. The crude argatroban obtained is then purified by extraction with chloroform, treatment with a saturated sodium bicarbonate solution and, after solvent evaporation, re-crystallization from ethanol or from 15% alcohol in water. It should be noted however that the Japanese patent makes no mention of the monohydrate form of argatroban being obtained and that for the compound the following characteristics are reported: m.p. 188-191° C.; molecular composition (theoretical/found) (%): C 54.31/54.01; H 7.13/6.98; N 16.52/16.61; I.R. (KBr) (cm$^{-1}$) 3400; 1620; 1460; 1380. These analytical data, with the exception of the unreported melting point, are the same as those indicated in the cited patent documents describing a mixture of (2R,4R)-4methyl-[4$N^2$-(3S-methyl-1,2,3,4-tetrahydro-8-quinolinesulphonyl)-L-arginyl]-2-piperidine carboxylic acid and (2R,4R)-4methyl-1-[$N^2$-(3R-methyl-1,2,3,4-tetrahydro-8-quinolinesulphonyl)-L-arginyl]-2-piperidine carboxylic acid isomers of argatroban, but do not correspond to the melting point given in the publication, being the only document that identifies the monohydrate form of argatroban.

More recently, patent application CN 1,951,937 (filing date 10 Nov. 2006) described a method for preparing hydrated argatroban by treating argatroban with large quantities of water (more than 60 and up to 80 volumes of distilled water per gram of argatroban) at a temperature of 80-100° C. for a time of 0.5-1 hour and crystallization by cooling. The water content reported is comprised between 3.3 and 3.8% and the ratio of dextroisomer R to levoisomer S is R:S=63-67:37-33.

Argatroban is a compound of wide therapeutic use, for which reason the need still exists to provide a compound of pharmaceutically acceptable quality obtained by easily industrialized and economically convenient methods. With regard to the monohydrate, this form is preferable for the applicative purpose since the anhydrous form is unstable and tends to become hydrated and/or wet. Moreover it crystallizes only with difficulty at the correct ratio between the diastereoisomers.

A first main purpose of the present invention is therefore to provide a method for preparing argatroban monohydrate usable as active principle of pharmaceutical quality for the preparation of proprietary drugs. A further purpose is to obtain said active principle by a synthesis and purification process which enables it to be obtained with a good yield and very high purity.

SUMMARY

For the previously indicated purposes the preparation method of argatroban monohydrate according to the invention consists of preparing crude argatroban, preferably starting from the compound (2R,4R)-1-[$N^G$-nitro-$N^2$-(3-methyl-8-quinolinesulphonyl)-L-arginyl]-4-methyl-2-piperidine carboxylic acid according to the known synthesis process of catalyzed hydrogenation and hydrogenolysis, then treating it to be purified and separated from the reaction mass into the monohydrate form by controlled crystallization in a methanol/water solvent. Preferably argatroban monohydrate is prepared by separating an intermediate consisting of purified argatroban which is then treated to be transformed into the monohydrate form by the previously mentioned process of crystallization from methanol/water. The preparation by separation of the purified intermediate is to be preferred, as this intermediate presents new and distinctive characteristics and allows argatroban monohydrate to be obtained with high purity and with the correct diastereoisomer ratio.

Furthermore, it has been surprisingly found that an argatroban anhydrous having new and distinctive physico-chemical characteristics can be subsequently obtained from argatroban monohydrate.

In a first aspect the invention hence relates to the preparation of argatroban monohydrate and optionally to argatroban anhydrous.

Therefore, the present invention provides a method for preparing argatroban monohydrate comprising at least the step of:

separating argatroban monohydrate from a concentrated reaction mass containing crude argatroban or from a purified argatroban by crystallization from a medium solvent consisting of methanol and water by adding a decolorizing carbon, heating the mass at the reflux temperature then subjecting it to carbon filtering and to controlled and gradual cooling from the reflux temperature to a temperature between 15-25° C. in a time comprised between 11-17 hours.

When the method of preparation is from a crude argatroban, according to a first embodiment of the invention, said method is substantially in one continuous step, but the argatroban monohydrate can be also prepared in two steps with isolation of a purified argatroban by crystallization from an organic solution of crude argatroban with a crystallization solvent selected from isopropanol and normal-propanol before separating the argatroban monohydrate by crystallization.

According to this second embodiment, the method of preparing argatroban monohydrate comprises at least the following steps of:

concentrating a reaction mass containing crude argatroban to a stirrable residue;

dissolving the residue containing crude argatroban with an organic solvent and separating a purified argatroban by crystallization by treating the organic solution with a crystallization medium solvent selected from isopropanol and normal-propanol;

separating argatroban monohydrate by re-crystallizing the purified argatroban isolated in the preceding step from a methanol and water mixture solution by adding a decolorizing carbon, heating the mass at the reflux temperature then subjecting it to carbon filtering and to controlled and gradual cooling from the reflux temperature to a temperature between 15-25° C. in a time comprised between 11-17 hours.

The crystalline precipitate consisting of argatroban monohydrate, obtained either by the continuous mode or in two steps by separating the purified argatroban intermediate, can be dried under nitrogen flow or under vacuum at a temperature comprised from 50° C. and 80° C. for at least 8 hours.

By subjecting the obtained argatroban monohydrate to re-crystallization from water by quickly cooling to a temperature of 15° C. in a time not greater than 2 minutes, argatroban anhydrous can be obtained, shown to possess new physico-chemical characteristics.

In a second aspect, therefore, the invention relates to the obtained and isolated single forms of argatroban and hence to: argatroban monohydrate, purified argatroban and argatroban anhydrous having the physico-chemical characteristics described below and reported in the claims that follow.

The advantages attainable with the present invention will be clear to an expert of the art from the following detailed description of particular embodiments of the method and from the compounds obtainable therewith given as non-limiting examples, with reference to the following figures.

DETAILED DESCRIPTION OF THE INVENTION

Figure 1:
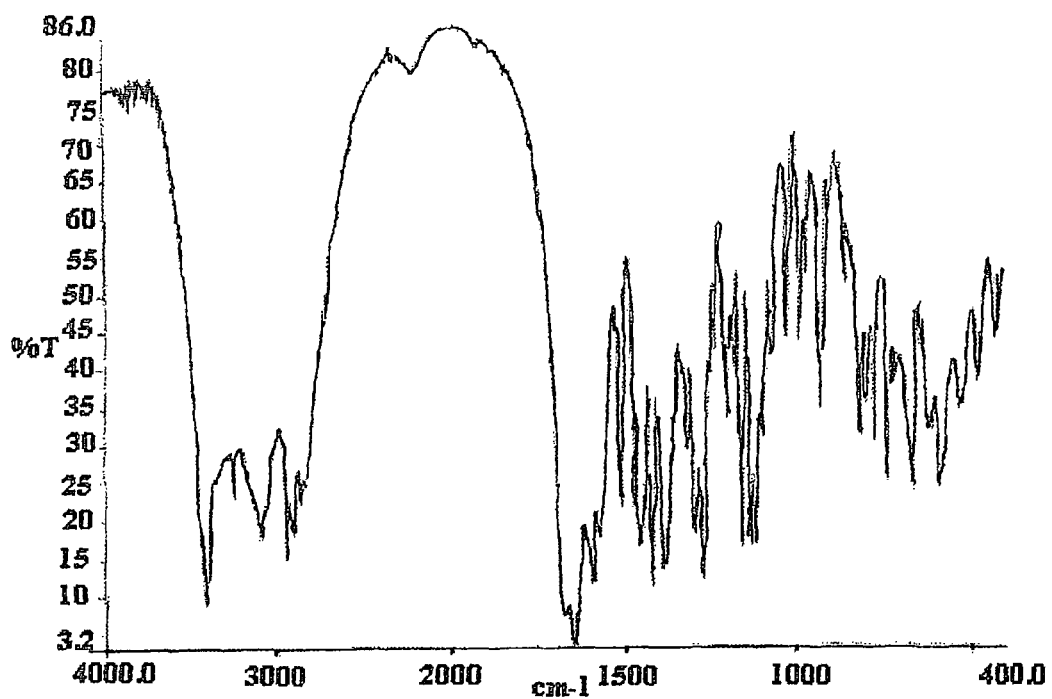
FIG. 1: the figure shows a representative I.R. spectrum of crystalline argatroban monohydrate obtained by crystallization from a solvent consisting of methanol and water according to the described method.

The process for preparing argatroban monohydrate of the present invention derives from the following scheme:

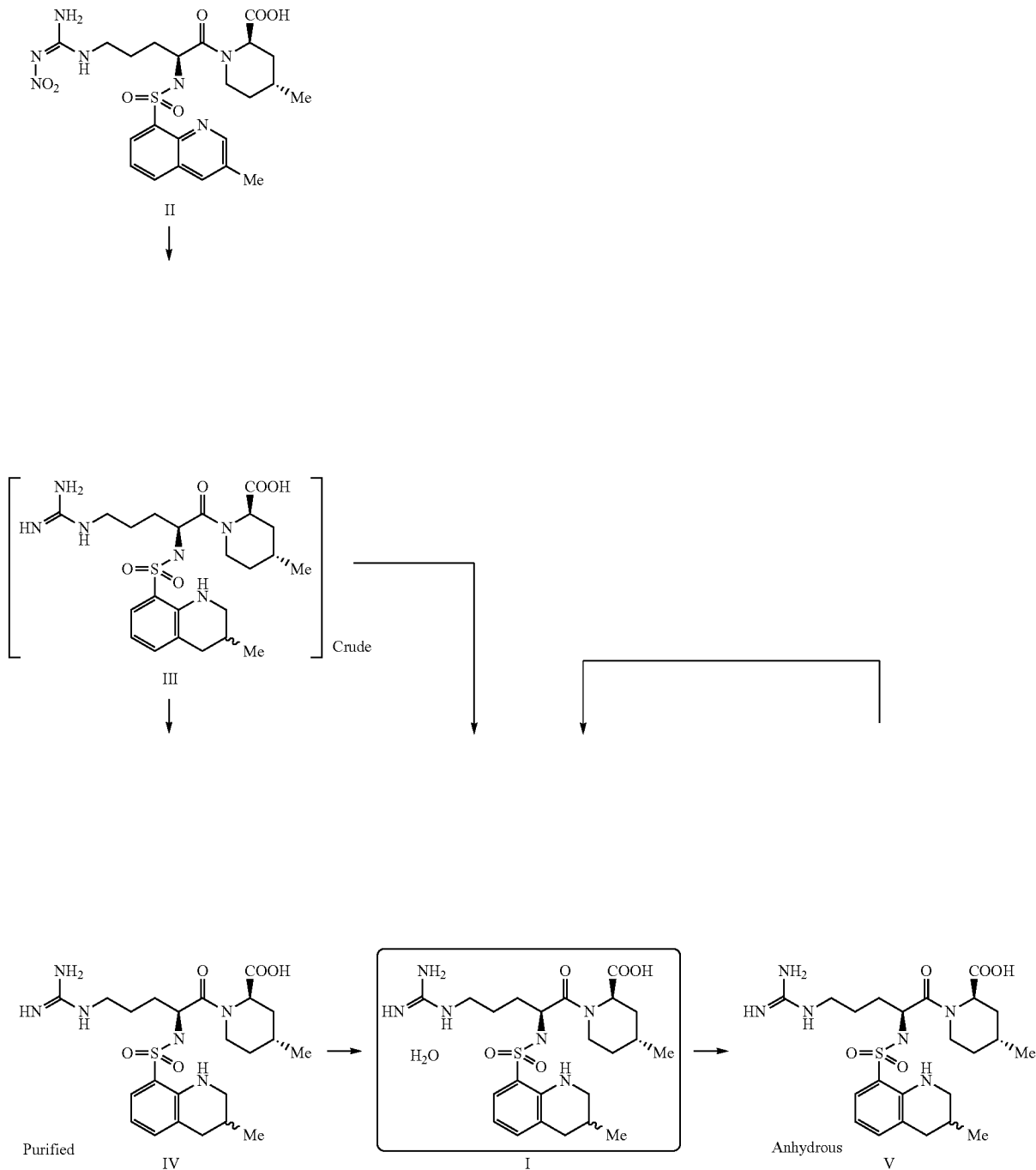

In the argatroban monohydrate preparation method of the invention, comprising the steps reported in the Summary, the starting compound for preparing argatroban monohydrate is (2R,4R)-1-[N$^G$-nitro-N$^2$-(3-methyl-8-quinolinosulphyl)-L-arginyl]-4-methyl-2-piperidine carboxylic acid (II) already described in U.S. Pat. No. 4,258,192 and EP 8746.

For the purposes of the present invention said compound (II) is subjected to a hydrogenation and hydrogenolysis catalyzed by a catalyst consisting of palladium on carbon (Pd/C) in a solvent formed from methanol in the presence of acetic acid in which the v/v ratio between the two is comprised between 1 (acetic acid) and 4-16 (alcohol) and the ratio between the starting compound (II) and acetic acid in w/v is comprised between 0.5 and 2.5. The hydrogenation reaction is conducted under hydrogen atmosphere in the manner known to an expert skilled in the art and preferably at a pressure from 6 to 12 bar and at temperatures from 50° C. to 100° C. for a time comprised between 6 and 18 hours.

Continuous Mode Process

When the process is in the continuous mode, after cooling to room temperature, the Pd/C catalyst is removed from the reaction mass, said obtained mass then being heated to temperatures between 40° C. and 80° C. and concentrated to at least half its volume.

The mixture thus obtained can be optionally treated with an aqueous solution of a base preferably chosen from sodium hydroxide, sodium bicarbonate and ammonia at a concentration between 10 and 30%, to bring the pH of the mixture itself to between 7.0 and 7.5.

The solution thus obtained is diluted with water to obtain a crystallization solvent for argatroban monohydrate (I) formed of a mixture of water and methyl alcohol in which the methyl alcohol has a concentration between 10 and 20%. The MetOH:water crystallization solvent is in a quantity up to 50 volumes per gram of argatroban (III) and preferably up to 40 volumes and more preferably comprised from 25 to 35 volumes, the MetOH:water ratio being preferably 1:7 v/v. Crystallization is subsequently achieved by: adding a decolorizing carbon, heating the mass at the reflux temperature and maintaining it under stirring for a time comprised between 1 and 3 hours followed by filtering the carbon and controlled cooling for a time comprised between 11-17 hours to bring the mixture from reflux temperature to 15-25° C., but preferably to 20° C. In particular the mass is subjected to the following temperature gradient: heating to 90-95° C., maintenance at reflux temperature from 1 to 3 hours, preferably for 2 hours, cooling to 70-75° C. in at least one hour and maintenance at this temperature for at least one hour, cooling to 20° C. in a time comprised between 2 and 6 hours, preferably in 4 hours, and maintenance at this temperature for at least 6 hours. The crystalline precipitate which forms is argatroban monohydrate (I) with the physico-chemical characteristics described hereinafter.

Considering all the step hereinabove reported in this first embodiment the preparation method of argatroban monohydrate comprises the steps of:
  preparing the crude argatroban from (2R,4R)-1-[N$^G$-nitro-N$^2$-(3-methyl-8-quinolinesulphonyl)-L-arginyl]-4-methyl-2-piperidine carboxylic acid in methanol/acetic acid;
  concentrating the reaction mass up to at least half of the volume;
  optionally treating the reaction mass with an aqueous solution of a base to bring the pH of the mixture itself to between 7.0 and 7.5;
  crystallizing the argatroban monohydrate by forming a crystallization medium solvent consisting of a mixture of methanol:water, wherein the methyl alcohol has a concentration between 10 and 20%, and subjecting the mass to an addition of carbon and to a heating at the reflux temperature then subjecting it to carbon filtration and to controlled and gradual cooling from the reflux temperature to a temperature between 15-25° C. in a time comprised between 11-17 hours.

In particular, the controlled and gradual cooling is at the following temperature gradient: heating to 90-95° C., maintenance at reflux temperature for a time between 1 and 3 hours, cooling to 70-75° C. in at least one hour and maintenance at this temperature for at least one hour, cooling to 20° C. in a time comprised between 2 and 6 hours and maintenance at this temperature for at least 6 hours.

A step of drying under nitrogen flow or under vacuum at a temperature comprised from 50° C. and 80° C. for at least 8 hours can be further comprise.

Process with Isolation of the Purified Argatroban (IV) Intermediate

The synthesis reaction is conduced as aforedescribed and on completion of hydrogenation, after cooling to room temperature, the Pd/C catalyst is removed from the obtained mass. Said mass is then heated to a temperature from 40° C. to 80° C. and concentrated to at least a stirrable residue.

The residue containing crude argatroban (III) is dissolved in an organic solvent, being preferably dichloromethane.

The mixture thus obtained can be optionally treated with an aqueous solution of a base preferably chosen from sodium hydroxide, sodium bicarbonate and ammonia at a concentration between 10 and 30%, to bring the pH of the mixture itself to between 7.0 and 7.5. Optionally in case of excess, the base is then removed either by washing the organic phase with water or under vacuum.

In this case a crystallization solvent selected from isopropyl alcohol and normal-propyl alcohol is added to the obtained mixture after treating the crude argatroban (III) with a base. Preferably for the purposes of the present invention the crystallization solvent is isopropyl alcohol; the mixture is heated to the solvent reflux temperature, the chlorinated solvent being removed by distillation, then cooled to 0-20° C. In this step, purified argatroban (IV) is obtained which, from the analyses carried out, proves to be solvated with the crystallization alcohol, in particular isopropanol, and has the physicochemical characteristics described below.

This crystalline precipitate is then treated to obtain argatroban monohydrate (I) as previously described after solubilization of the purified argatroban (IV) in a methanol:water mixture as previously described.

Separation of the purified argatroban by crystallization from normal-propanol or isopropanol allows a more efficient preparation in terms of argatroban monohydrate yield and purity and moreover a better processability of the product and reliability of the process, as propanol alcohols are better for these aspects than ethanol. As a crystallization solvent, ethanol, in case of even slight volumetrical errors, can actually cause significant yield reductions with negative consequences on the diastereoisomer ratio. This would lead to greater difficulties in achieving the correct diastereoisomer ratio in the subsequent crystallization. With methanol, this effect is accentuated. The solvate obtained, indicated herein as purified argatroban, as well as being new, instead exhibits crystalline characteristics such as to greatly facilitate its purification and isolation without negatively affecting the diastereoisomer ratio.

Considering all the step hereinabove reported in this second embodiment the preparation method of argatroban monohydrate comprises the steps of:

preparing the crude argatroban from (2R,4R)-1-[N$^G$-nitro-N$^2$-(3-methyl-8-quinolinesulphonyl)-L-arginyl]-4-methyl-2-piperidine carboxylic acid in methanol/acetic acid;

optionally treating the reaction mass with an aqueous solution of a base to bring the pH of the mixture itself to between 7.0 and 7.5;

concentrating the reaction mass containing crude argatroban to a stirrable residue;

dissolving the residue containing crude argatroban with an organic solvent and separating the purified argatroban by crystallization by treating the organic solution with a crystallization solvent selected from isopropanol and normal-propanol;

separating argatroban monohydrate by re-crystallizing the purified argatroban isolated in the preceding step from a solvent medium consisting of a mixture of methanol: water, wherein the methyl alcohol has a concentration between 10 and 20%, and subjecting the mass to an addition of decolorizing carbon, a heating at the reflux temperature then subjecting it to carbon filtration and controlled and gradual cooling to a temperature between 15-25° C. in a time comprised between 11-17 hours.

In particular, the controlled and gradual cooling is at the following temperature gradient: heating to 90-95° C., maintenance at reflux temperature for a time between 1 and 3 hours, cooling to 70-75° C. in at least one hour and maintenance at this temperature for at least one hour, cooling to 20° C. in a time comprised between 2 and 6 hours and maintenance at this temperature for at least 6 hours.

A step of drying under nitrogen flow or under vacuum at a temperature comprised from 50° C. and 80° C. for at least 8 hours can be further comprise.

The preparation method of the argatroban monohydrate according to the invention proves to fulfill the purposes of the same.

In fact, the yields of argatroban monohydrate obtained, either in the case of a continuous step or a two step preparation, are between 65% and 70%; the obtained compound has shown a purity at least equal to or higher than 99%, a KF of at least 3.4% and an isomer ratio of 65:35±2.

With regard to the purity, the argatroban monohydrate obtainable with the method according to the invention has an impurity profile where any single impurity is less than 0.1% and preferably below 0.03%. Accordingly the purity of the argatroban monohydrate is at least equal to or higher than 99.0% and preferably at least of or higher than 99.8%.

Optionally, argatroban anhydrous (V) can be obtained from argatroban monohydrate, this being obtained either in a continuous mode or in two distinct steps, by re-dissolving in water the obtained crystalline precipitate, consisting of argatroban monohydrate (I), heating the solution to a temperature between 75° and 100° C., preferably 80° C., removing the un-dissolved residues, then quickly cooling the solution to 10° C.-20° C., preferably to 15° C., in a time of 2 minutes and maintaining it at said temperature for a period of up to 1 hour.

The argatroban obtained in this manner is anhydrous and has the physico-chemical characteristics described hereinafter.

Characterization of Argatroban Monohydrate

The analytical data of (2R,4R)-4-methyl-1-[N$^2$-[(1,2,3,4-tetrahydro-3-methyl-8-quinolylsulphonyl]-L-arginyl]pipecolic acid monohydrate (I) are given below:

Empirical formula: $C_{23}H_{38}N_6O_6S$;
Molecular weight: 526.65;
Molecular composition:

|  | C | H | N | S |
|---|---|---|---|---|
| Calculated (%): | 52.45 | 7.27 | 15.96 | 6.09 |
| Found (%): | 52.46 | 7.30 | 15.95 | 6.11; |

Figure 2:
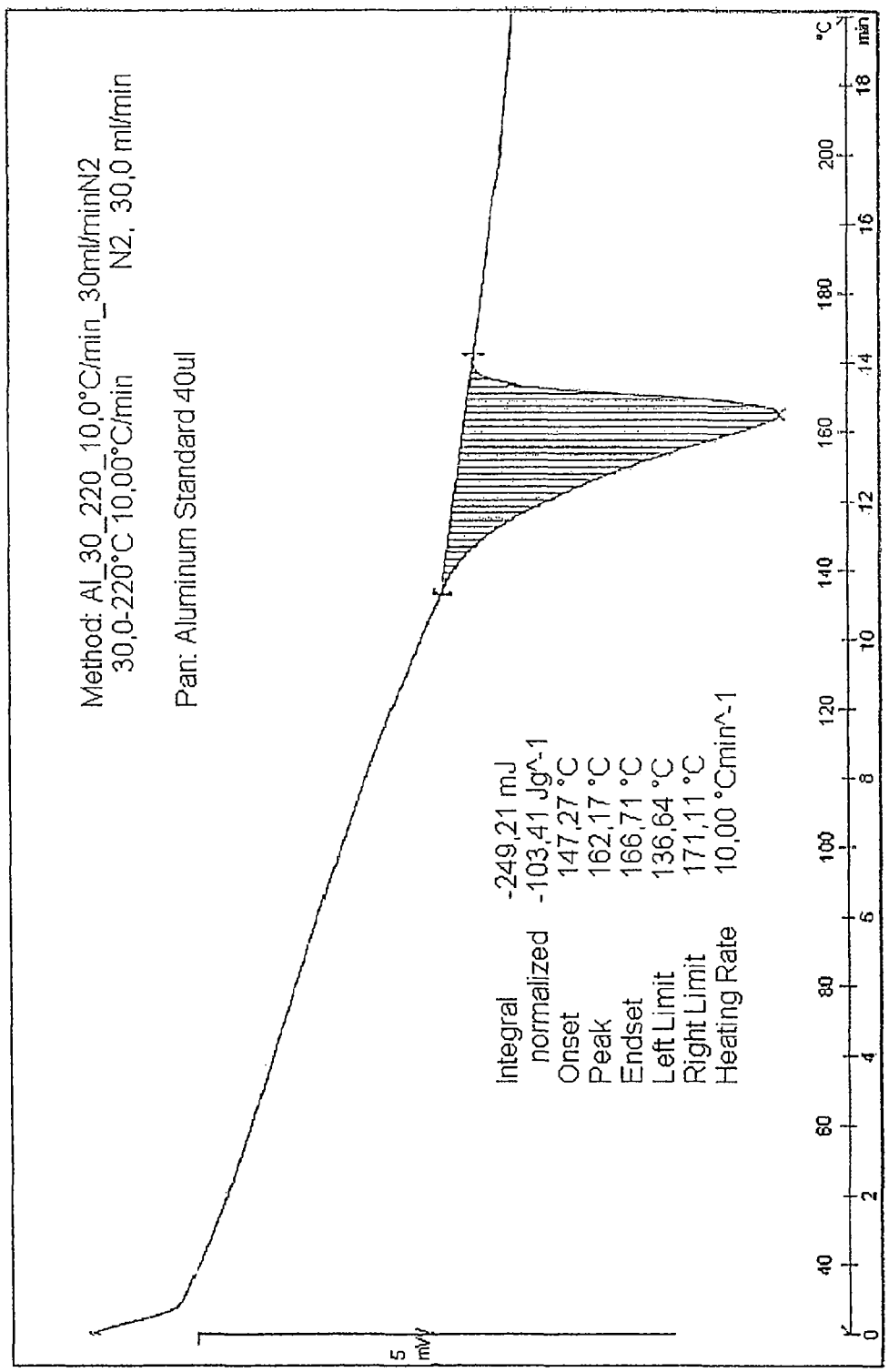
FIG. 2: the figure shows the differential scanning calorimetry (DSC) for a representative sample of argatroban monohydrate obtained by crystallization from a solvent consisting of methanol and water according to the described method.
Figure 3:
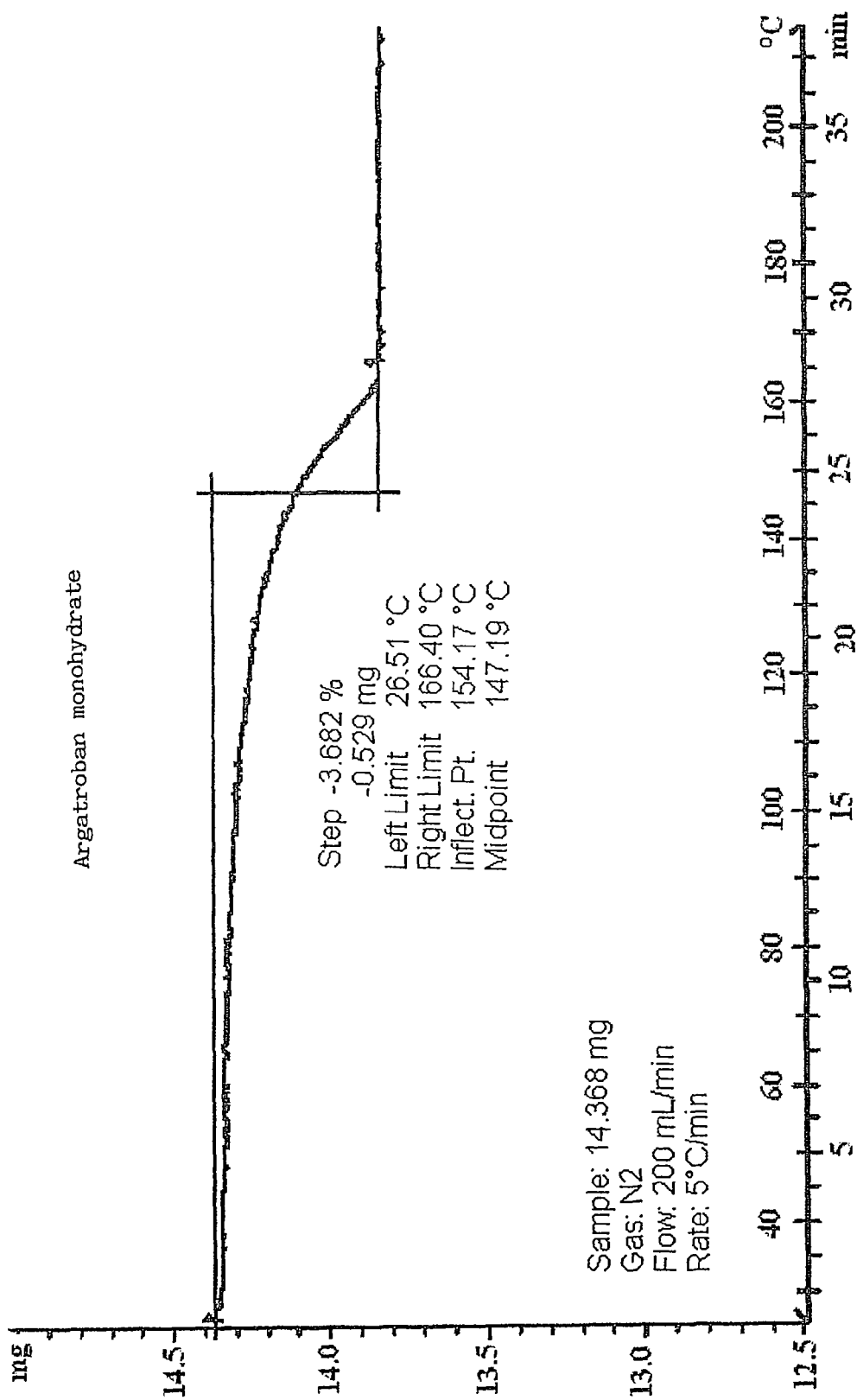
FIG. 3: the figure shows a thermogravimetric analysis of a representative sample of argatroban monohydrate obtained by crystallization from a solvent consisting of methanol and water according to the described method.
Figure 4:
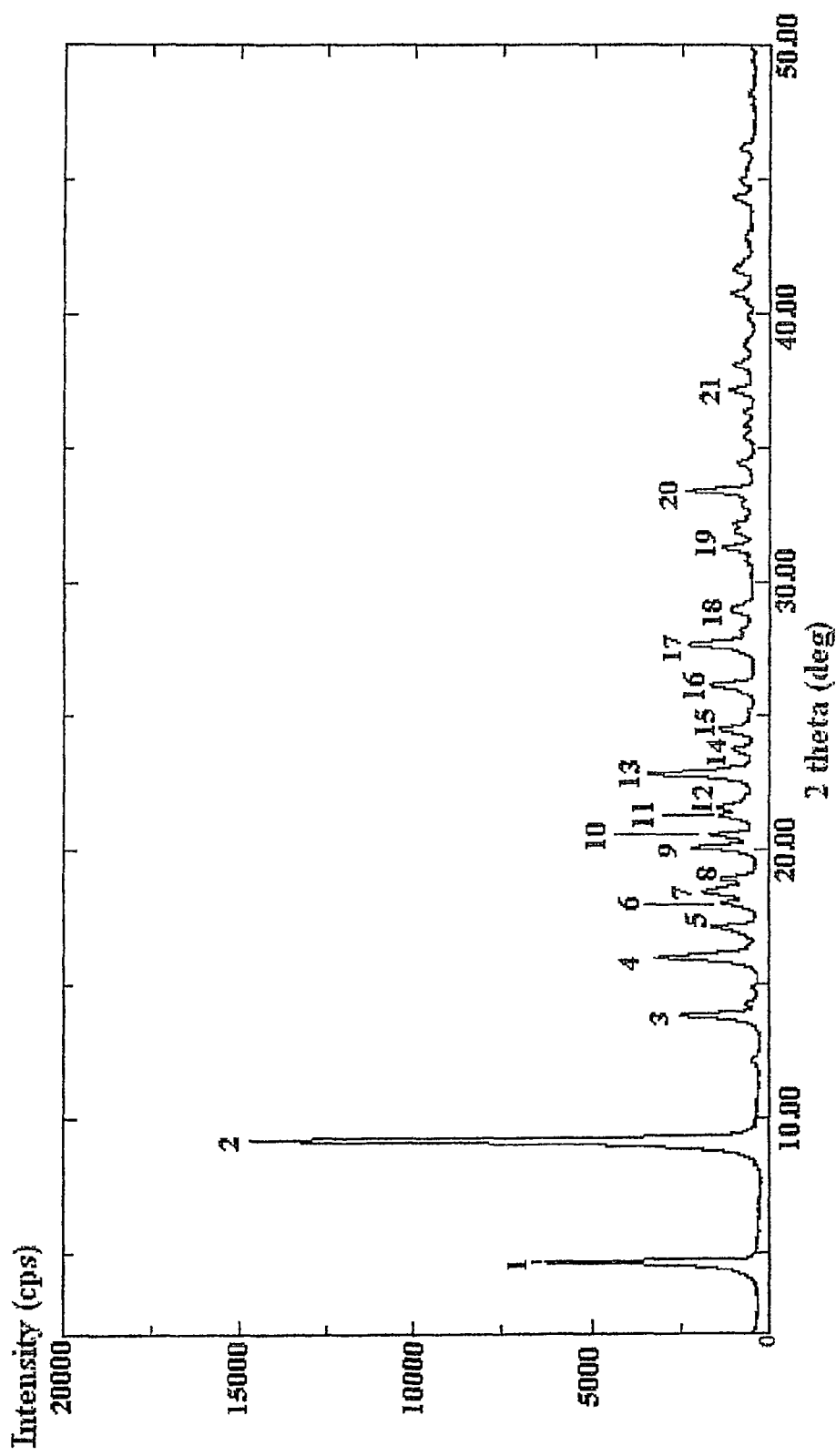
FIG. 4: the figure shows a diffractometry (XRPD) profile of argatroban monohydrate obtained by crystallization from a solvent consisting of methanol and water according to the described method.

Purity by HPLC: 99.0% -99.8%;

I.R. (KBr): 3416, 1272, 1157 cm$^{-1}$. A representative I.R. spectrum of argatroban monohydrate obtained by the described method is shown in FIG. 1;

Optical rotation power: $[\alpha]_D^{27}$=+78 (c=1 mg/ml in 0.2 N HCl);

Melting point: 176-182° C. Melting point was determined using glass capillary tubes;

Differential scanning calorimetry (DSC) and thermogravimetric analysis (TGA): Differential scanning calorimetry was carried out using a perforated aluminium crucible. The argatroban monohydrate shows an endothermic event at about 150° C. FIG. 2 gives a typical DSC profile. The endothermic phenomenon represents water loss and subsequent melting of the compound. Water loss is clearly demonstrated by the thermogravimetric analysis profile in FIG. 3. Thermogravimetric analysis shows that the compound appears as a monohydrate, as the water loss is 3.68% in a temperature range from 85-177° C., a value which totally fits the theoretical value of 3.42%. The high temperature range for weight loss, being greater than 175° C., also indicates that the nature of the contained water is of crystalline type;

Analysis by X-ray diffractometry: argatroban monohydrate appears as a white crystalline solid. The peaks relating to argatroban monohydrate and shown in FIG. 4 are summarized in the table 1 below:

TABLE 1

| Peak No. | Angle (2θ) | Relative intensity (%) |
|---|---|---|
| 1 | 4.680 | 43 |
| 2 | 9.230 | 100 |
| 3 | 13.850 | 18 |
| 4 | 15.980 | 23 |
| 5 | 17.120 | 12 |
| 6 | 18.040 | 10 |
| 7 | 18.430 | 14 |
| 8 | 18.950 | 10 |
| 9 | 20.080 | 16 |
| 10 | 20.560 | 12 |
| 11 | 21.260 | 10 |
| 12 | 21.590 | 11 |
| 13 | 22.820 | 24 |
| 14 | 23.740 | 8 |
| 15 | 24.480 | 11 |
| 16 | 26.140 | 12 |
| 17 | 27.620 | 16 |
| 18 | 28.980 | 8 |
| 19 | 31.320 | 10 |
| 20 | 33.440 | 17 |
| 21 | 37.210 | 8 |

Characterization of Argatroban Anhydrous

Figure 5:
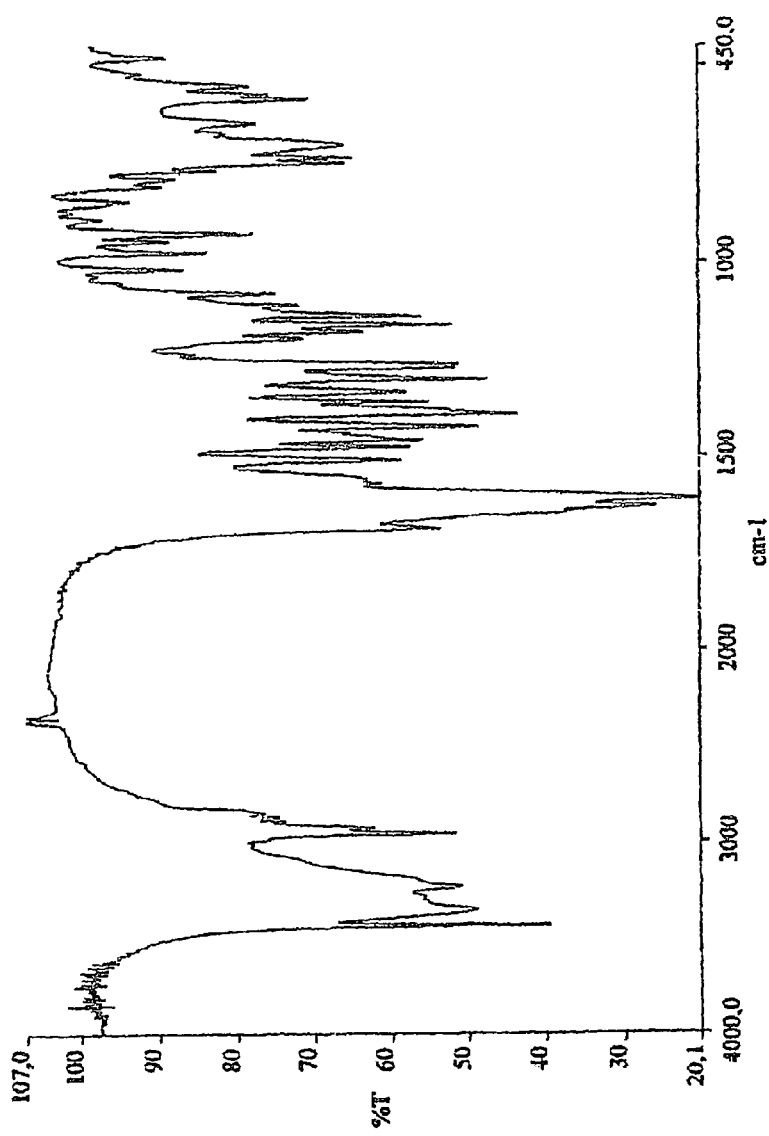
FIG. 5: the figure shows a representative I.R. spectrum of argatroban anhydrous obtained from argatroban monohydrate by the described method.
Figure 6:
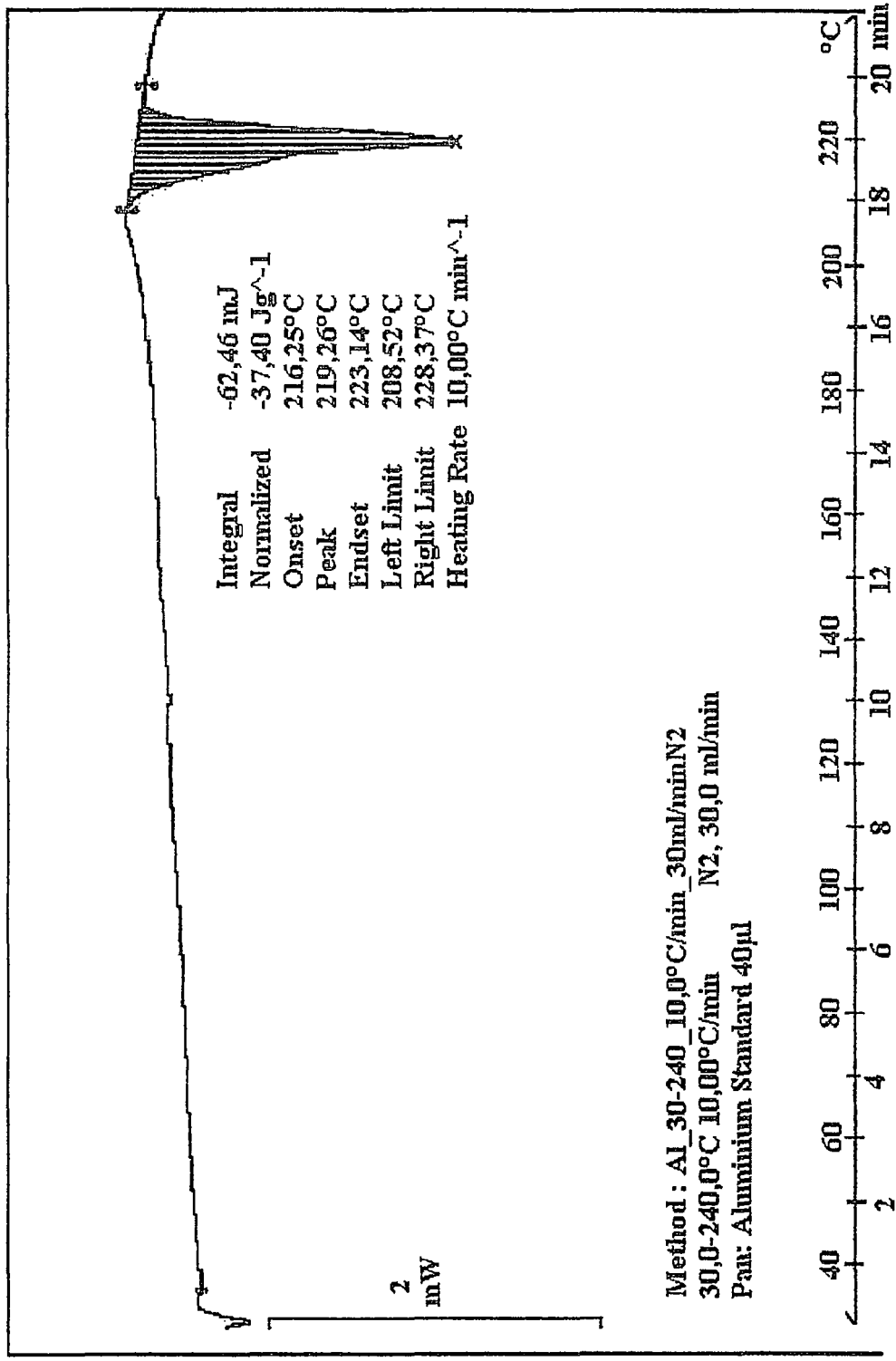
FIG. 6: the figure shows the differential scanning calorimetry (DSC) for a representative sample of argatroban anhydrous obtained from argatroban monohydrate by the described method.

The description of a representative sample of (2R,4R)-4-methyl-1-[N$^2$-[(1,2,3,4-tetrahydro-3-methyl-8-quinolyl)sulphonyl]-L-arginyl]pipecolic acid in anhydrous form (V), and a comparison with the corresponding monohydrate form are given below:

Molecular formula: $C_{23}H_{36}N_6O_5S$;
Molecular weight: 508.63;
Melting point: 220° C. with decomposition;
I.R. (KBr): 3432, 1265, 1164. A representative I.R. spectrum of the argatroban anhydrous obtained by the described method is shown in FIG. 5;

Differential scanning calorimetry (DSC) and thermogravimetric analysis (TGA): Differential scanning calorimetry and thermogravimetric analysis were carried out under the same conditions adopted for the argatroban monohydrate analysis. FIG. 6 gives a representative DSC analysis of an argatroban anhydrous sample. The argatroban anhydrous shows an endothermic event at about 215° C. The endothermic phenomenon is associated with melting of the compound.

Figure 7:
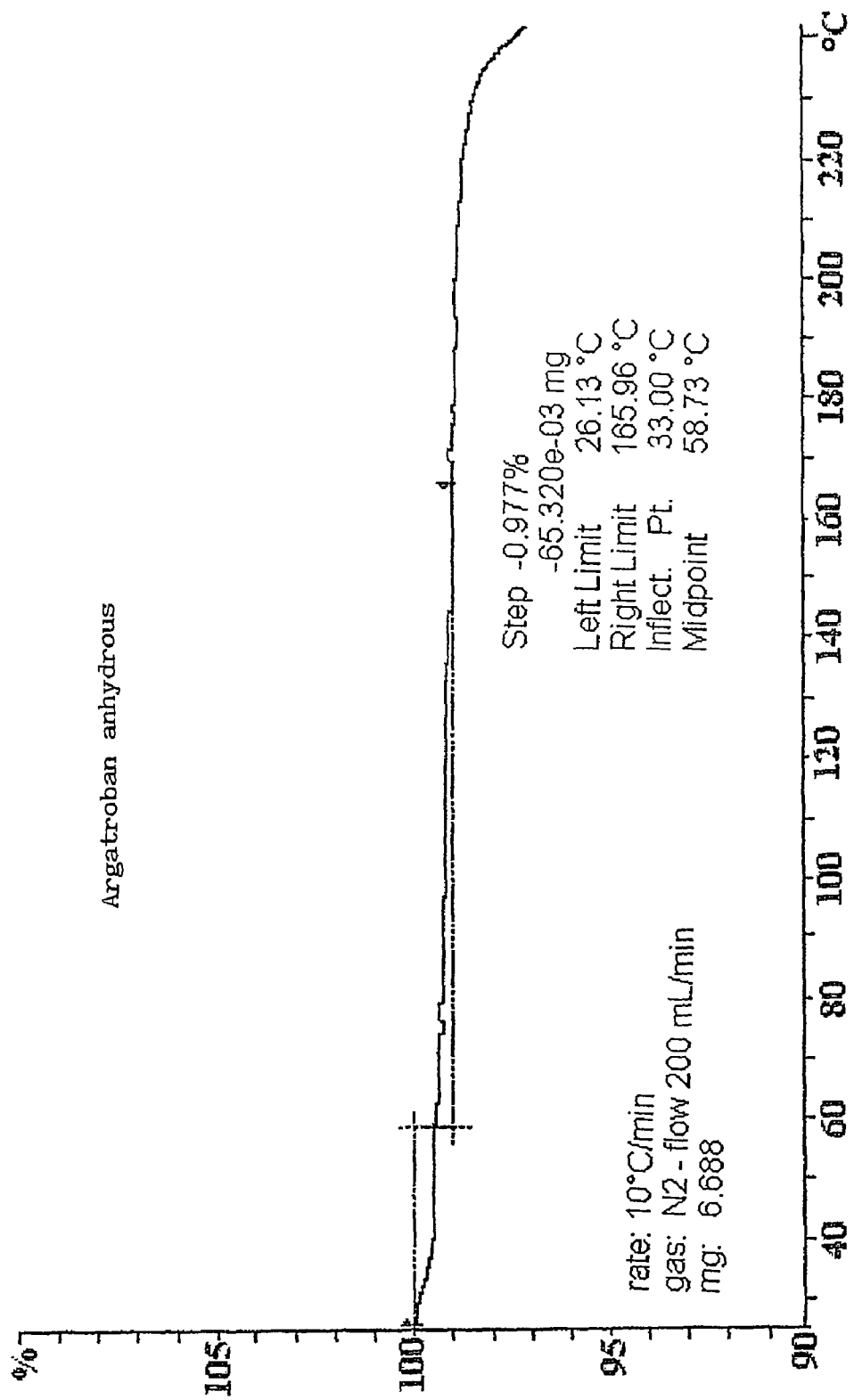
FIG. 7: the figure shows a thermogravimetric analysis of a representative sample of argatroban anhydrous obtained from argatroban monohydrate by the described method.
Figure 8:
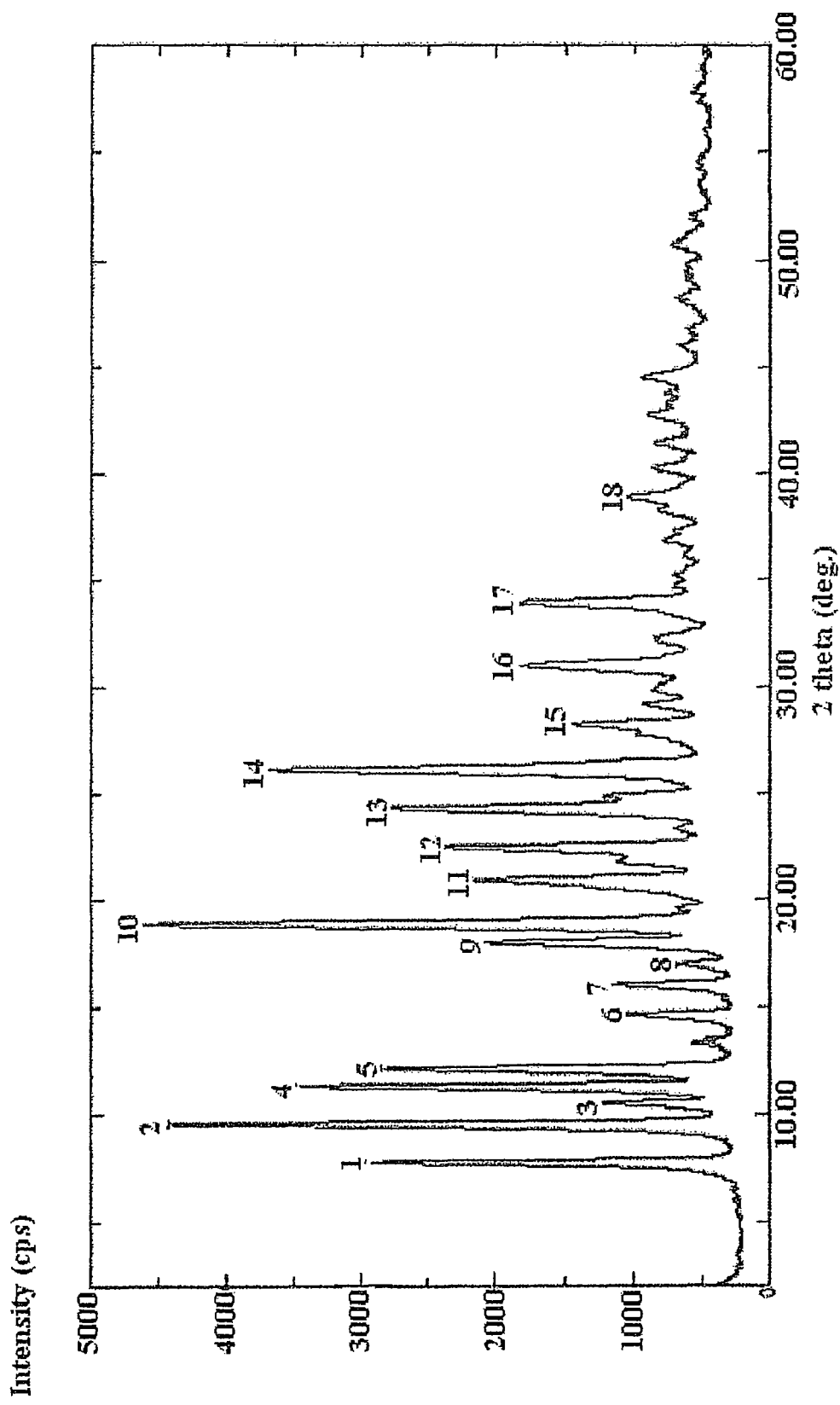
FIG. 8: the figure shows a diffractometry (XRPD) profile of argatroban anhydrous obtained from argatroban monohydrate by the described method.

The thermogravimetric analysis is shown in FIG. 7. The loss of around 1% in weight within a temperature range of between 25° and 140° C. is ascribable to the presence of a small quantity of water of imbibition;

X-ray diffraction: the XRPD analysis was carried out by following the procedure described for argatroban monohydrate. The following table 2 gives a summary of the peaks shown in FIG. 8:

TABLE 2

| Peak No. | Angle (2θ) | Relative intensity (%) |
| --- | --- | --- |
| 1 | 7.790 | 64 |
| 2 | 9.560 | 95 |
| 3 | 10.480 | 27 |
| 4 | 11.320 | 75 |
| 5 | 12.120 | 61 |
| 6 | 14.640 | 23 |
| 7 | 16.010 | 25 |
| 8 | 16.940 | 14 |
| 9 | 18.030 | 45 |
| 10 | 18.900 | 100 |
| 11 | 20.960 | 47 |
| 12 | 22.550 | 53 |
| 13 | 24.370 | 61 |
| 14 | 26.170 | 81 |
| 15 | 28.300 | 32 |
| 16 | 30.960 | 40 |
| 17 | 33.970 | 40 |
| 18 | 38.930 | 23 |

Characterization of Argatroban Solvated in Isopropanol

Figure 9:
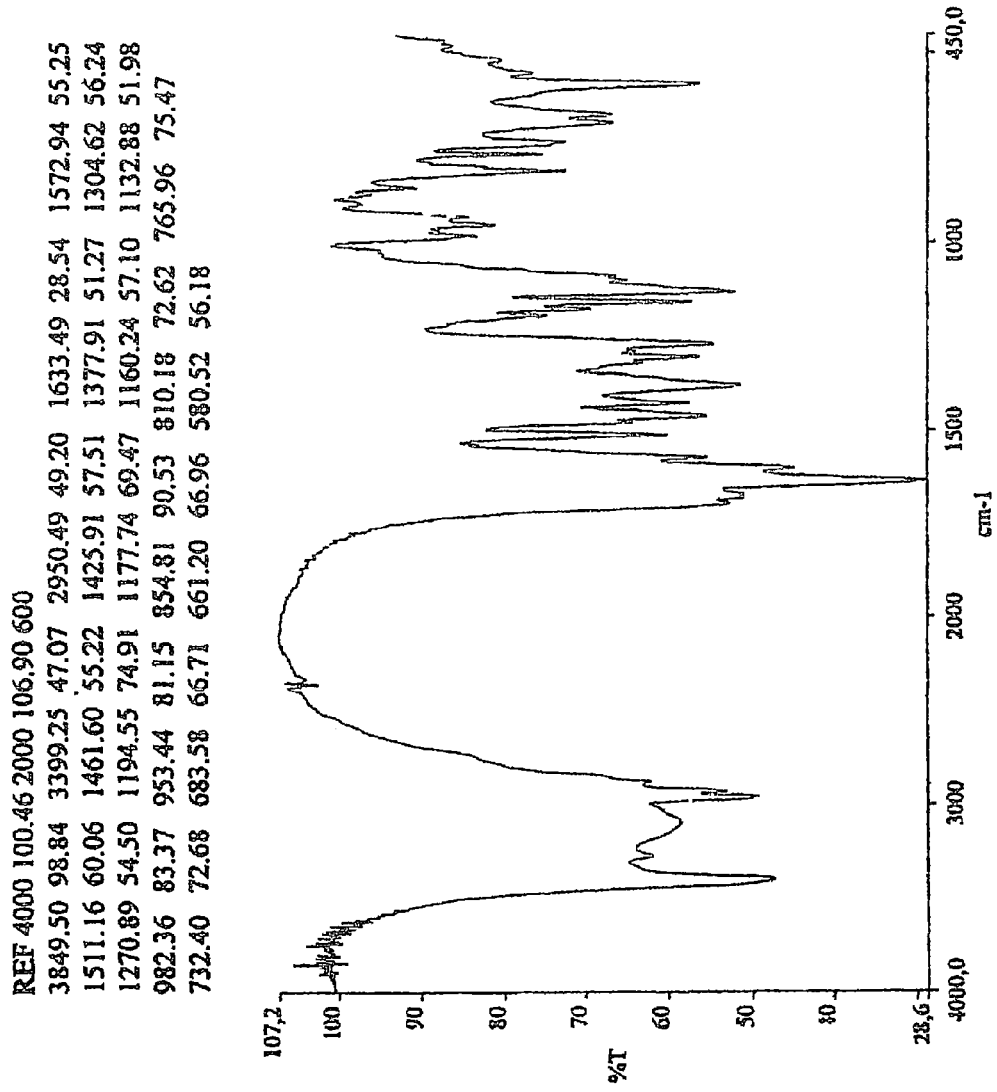
FIG. 9: the figure shows a representative I.R. spectrum of purified argatroban obtained by the described method.
Figure 10:
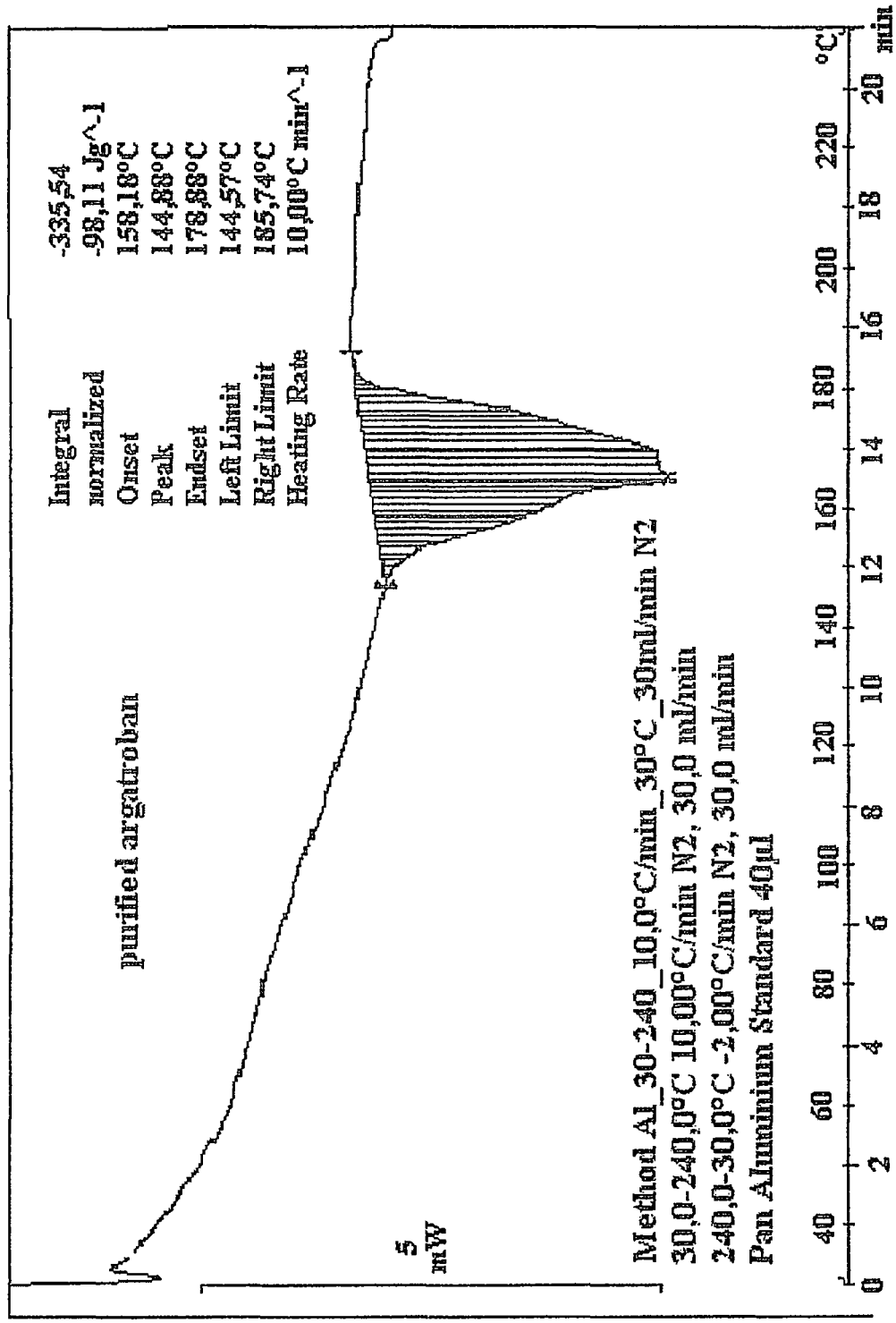
FIG. 10: the figure shows the differential scanning calorimetry (DSC) for a representative sample of purified argatroban obtained by the described method.
Figure 11:
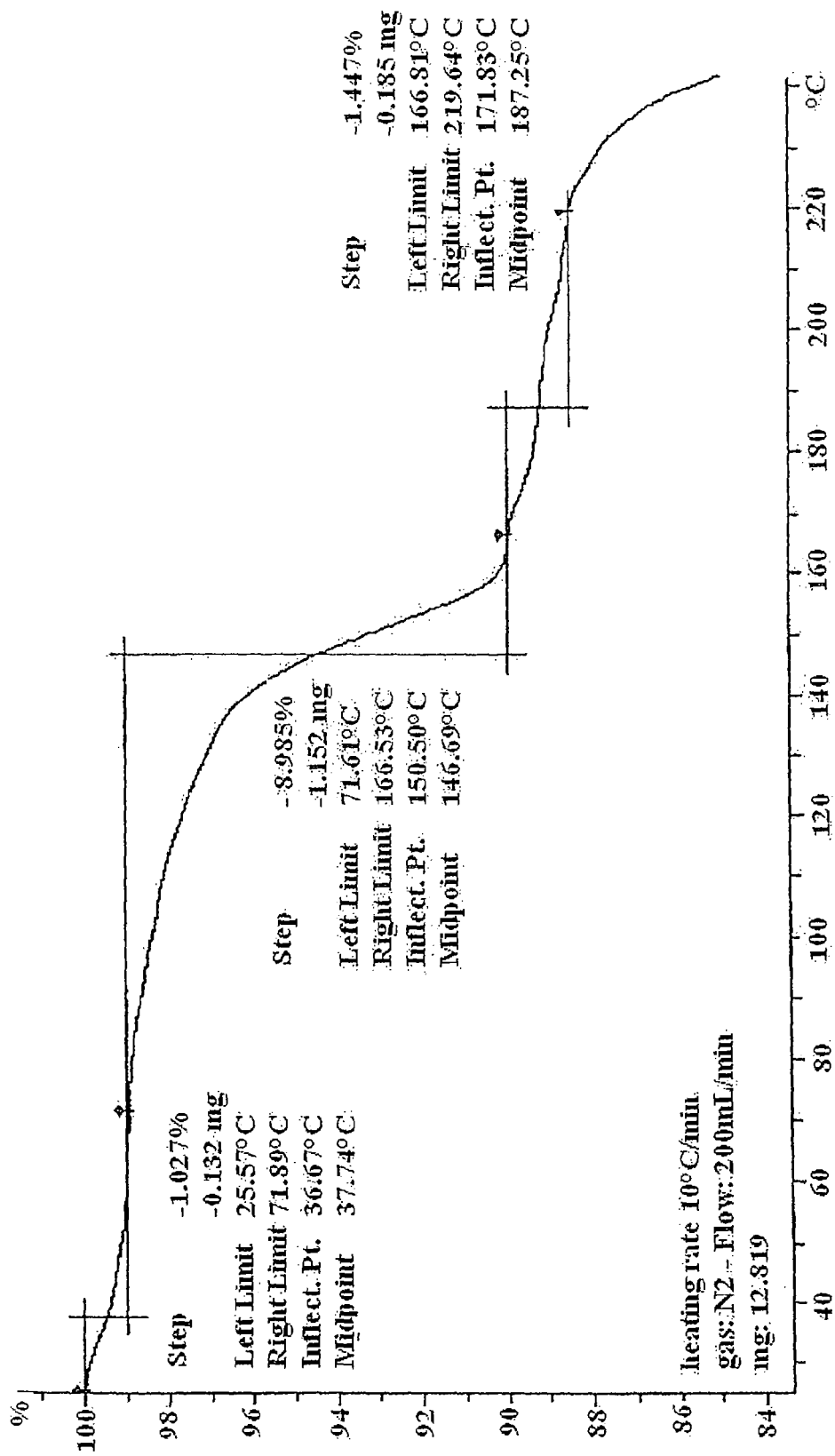
FIG. 11: the figure shows a thermogravimetric analysis of a representative sample of purified argatroban obtained by the described method.
Figure 12:
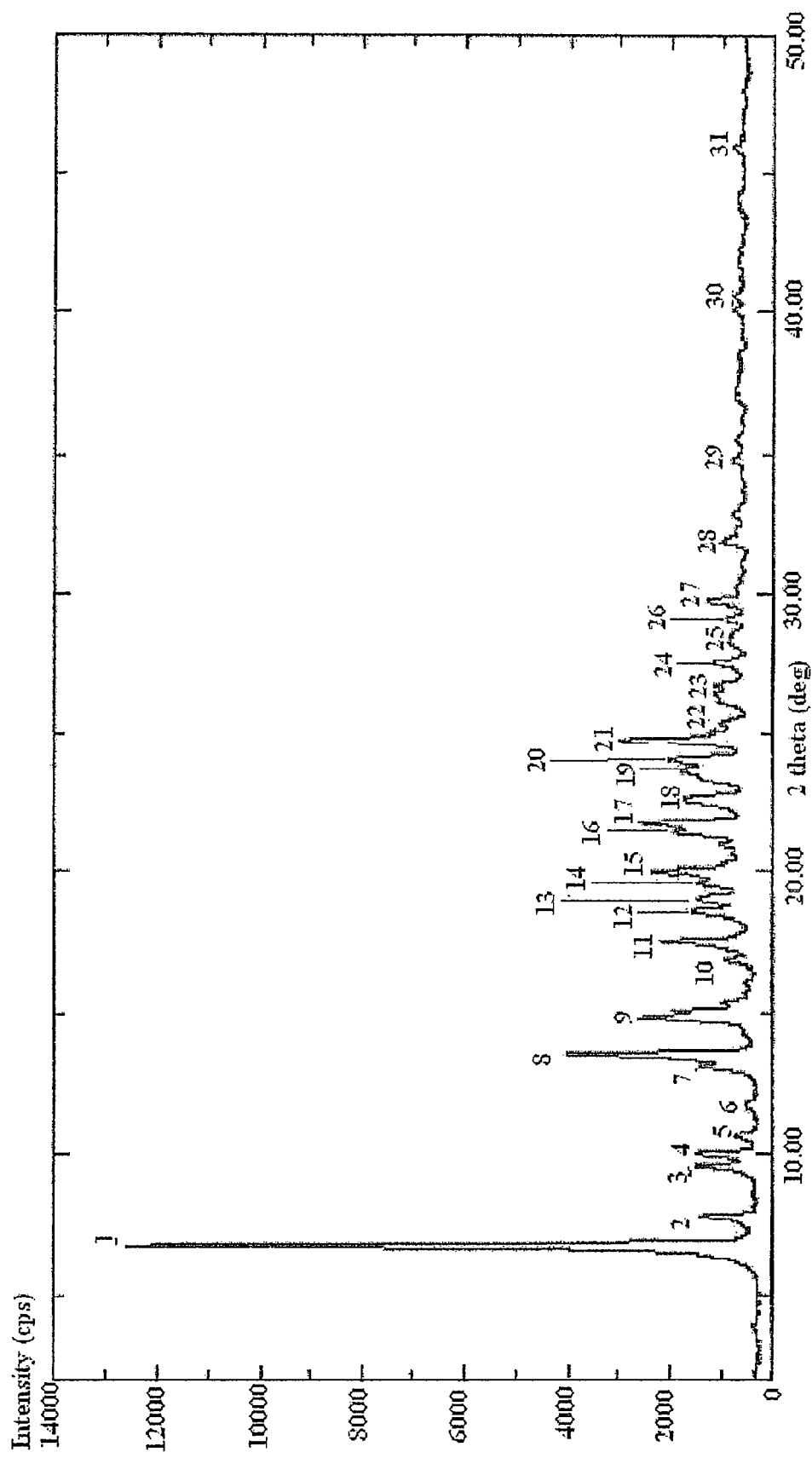
FIG. 12: the figure shows a diffractometry (XRPD) profile of purified argatroban.

The analytical data of purified (2R,4R)-4-methyl-1-[N$^2$-[(1,2,3,4-tetrahydro-3-methyl-8-quinolyl)sulphonyl]-L-arginyl]pipecolic acid (IV) solvated with isopropanol are given below:

I.R. (KBr): 3399, 1270, 1160 cm$^{-1}$. A representative I.R. spectrum of argatroban solvated with iPrOH obtained by the described method is given in FIG. 9;

Melting point: 183-185° C. Melting point determination was carried out using glass capillary tubes;

Differential scanning calorimetry (DSC) and thermogravimetric analysis (TGA): differential scanning calorimetry was carried out using a perforated aluminium crucible. The argatroban solvated with isopropanol has an endothermic peak at about 160° C. FIG. 10 gives a typical DSC profile. The endothermic event represents solvent loss and melting of the compound. Solvent loss is clearly demonstrated from the thermogravimetric analysis profile in FIG. 11. Thermogravimetric analysis shows that the compound appears as a solvate with isopropanol, as the solvent loss is 9.0%, a value which totally fits the theoretical value of 10.55% for a monosolvate form. The high temperature range for weight loss, being between 70° C. and 176° C., also indicates that the nature of the contained solvent is of crystalline type;

Analysis by X-ray diffraction: the argatroban solvated with isopropanol appears as a white crystalline solid. The peaks obtained for argatroban solvated with isopropanol and shown in FIG. 12 are summarized in the table 3 below:

TABLE 3

| Peak No. | Angle (2θ) | Relative intensity (%) |
| --- | --- | --- |
| 1 | 6.800 | 100 |
| 2 | 7.840 | 12 |
| 3 | 9.800 | 13 |
| 4 | 10.020 | 13 |
| 5 | 10.700 | 6 |
| 6 | 11.780 | 5 |
| 7 | 13.080 | 12 |
| 8 | 13.540 | 32 |
| 9 | 14.540 | 21 |
| 10 | 16.900 | 8 |
| 11 | 17.540 | 18 |
| 12 | 18.640 | 14 |
| 13 | 19.060 | 13 |
| 14 | 19.620 | 13 |
| 15 | 20.000 | 20 |
| 16 | 21.420 | 16 |
| 17 | 21.780 | 21 |
| 18 | 22.660 | 15 |
| 19 | 23.680 | 15 |
| 20 | 24.080 | 16 |
| 21 | 24.740 | 25 |
| 22 | 25.340 | 9 |
| 23 | 26.480 | 10 |
| 24 | 27.580 | 10 |
| 25 | 28.220 | 7 |
| 26 | 29.120 | 8 |
| 27 | 29.740 | 11 |
| 28 | 31.820 | 9 |
| 29 | 34.840 | 7 |
| 30 | 40.580 | 6 |

Figure 13:
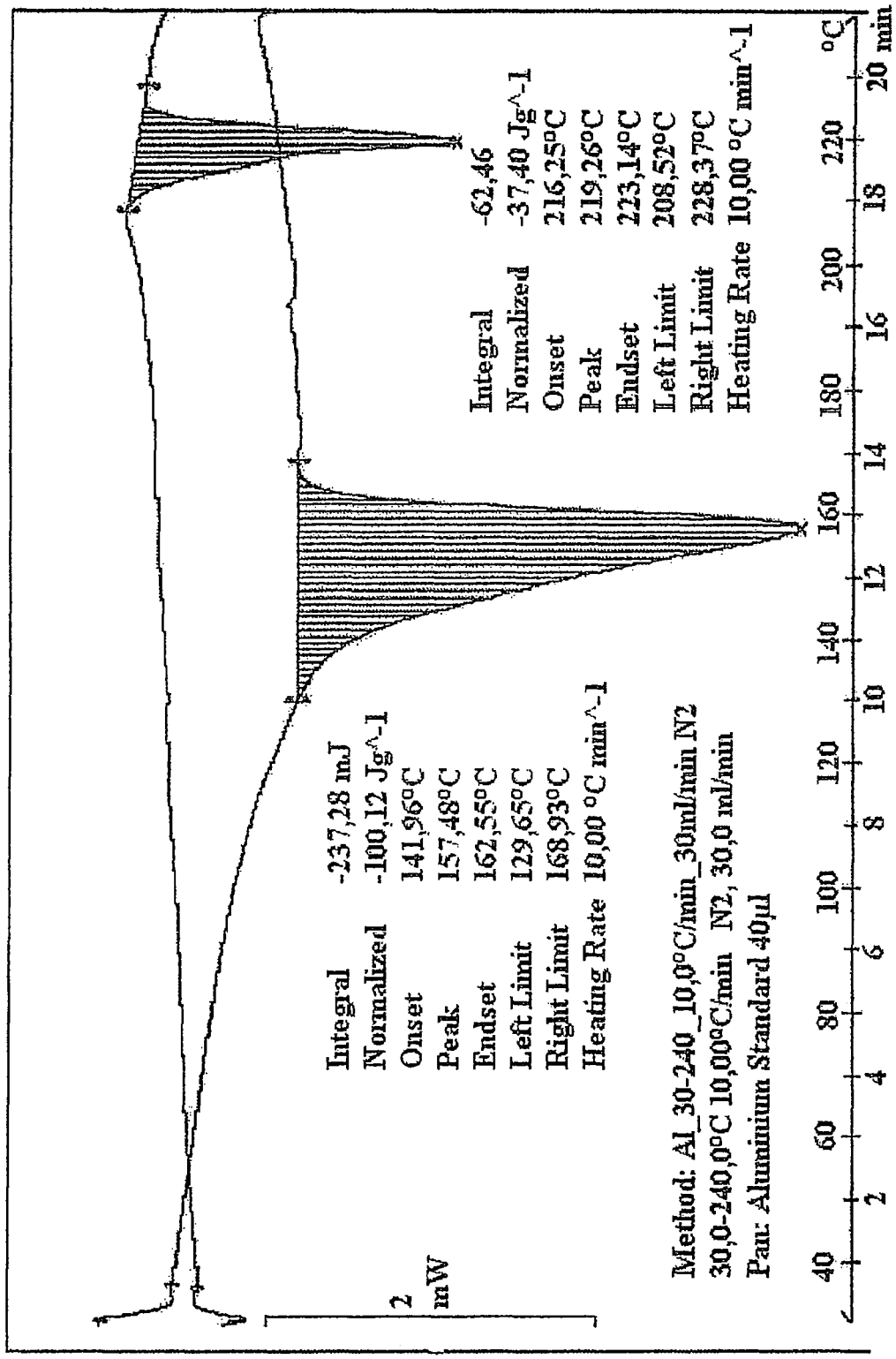
FIG. 13: the figure shows a comparison between the DSC for argatroban anhydrous (2° peak) and the corresponding monohydrate (1° peak) form obtained by the described method.

Comparison of Argatroban Monohydrate, Argatroban Anhydrous and Purified Argatroban Differential scanning calorimetry (DSC): as can be seen by comparison, the DSC profile of argatroban monohydrate differs considerably from the profile noted for the anhydrous compound. In this respect argatroban monohydrate has an endothermic peak at about 160° C. whereas that of argatroban anhydrous is shown at 220° C. (FIG. 13).

Figure 14:
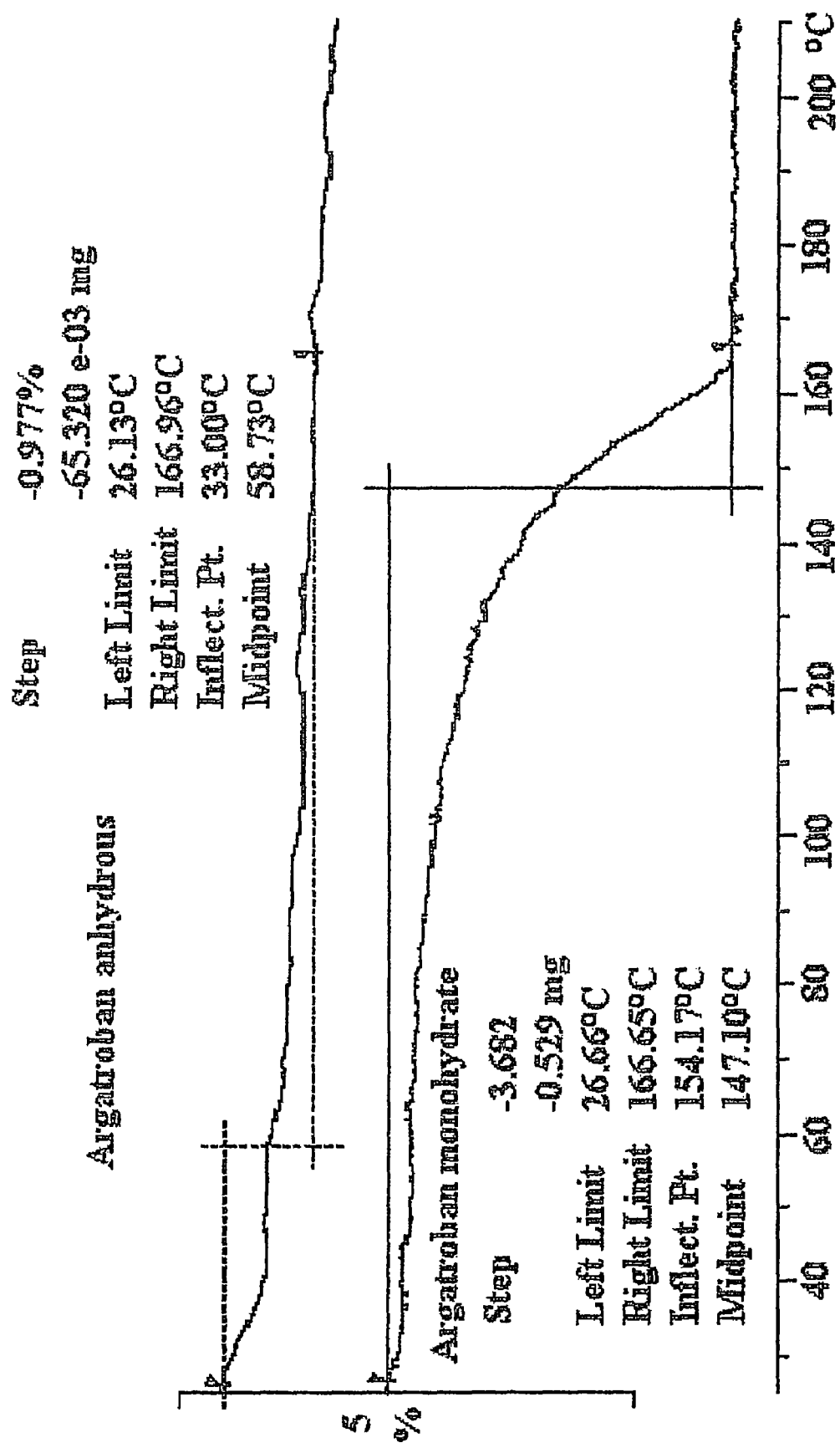
FIG. 14: the figure shows a comparison between the thermogravimetric analyses of argatroban anhydrous (upper curve) and monohydrate (lower curve) obtained by the described method.

Thermogravimetric analysis (TGA): with regard to the thermogravimetric analysis, a substantial difference between the curves of monohydrate and anhydrous argatroban can again be seen, indicating the fact that the respective weight losses are different in nature (FIG. 14).

Figure 15:
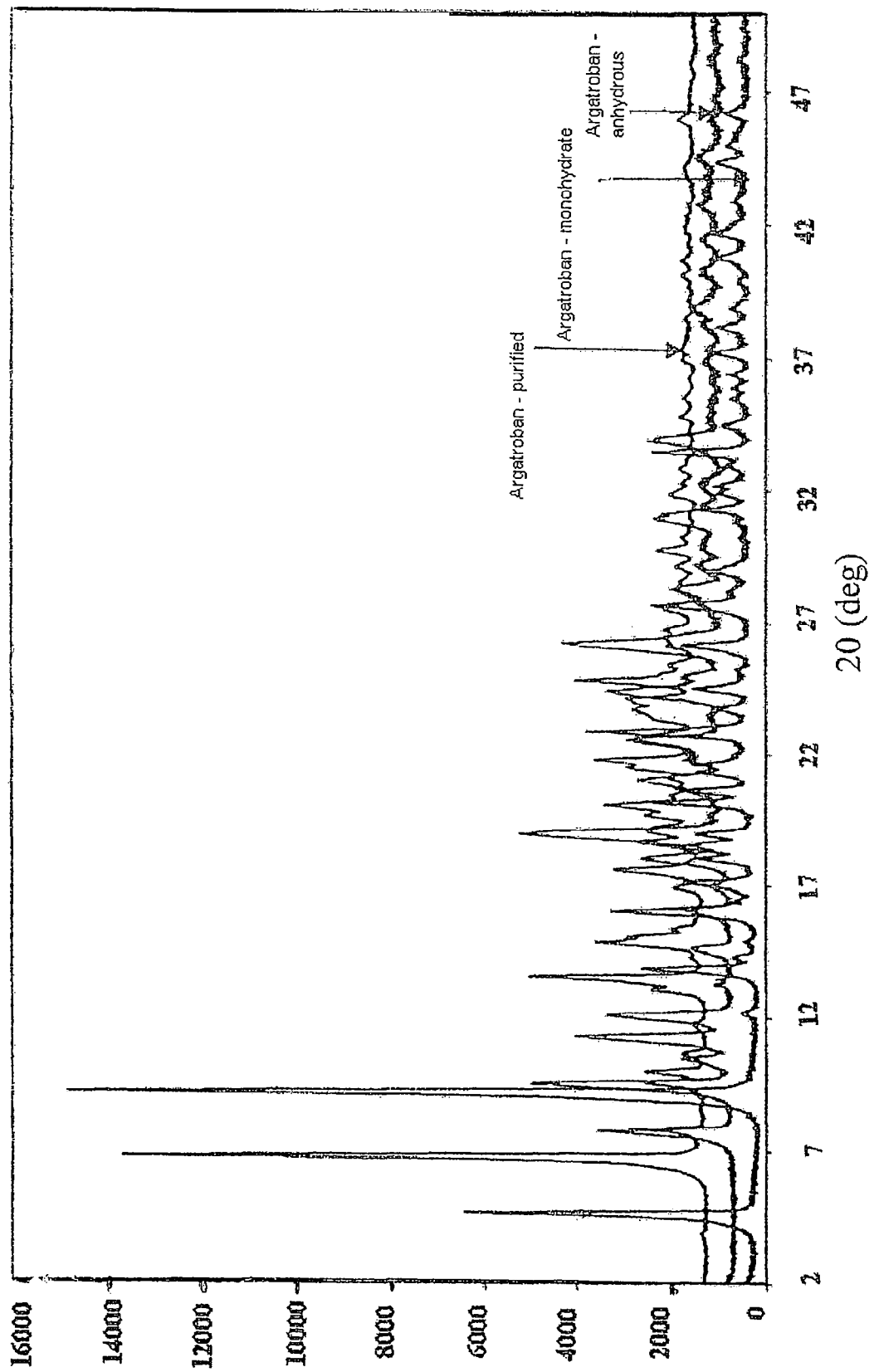
FIG. 15: the figure shows a comparison between the XRPD diffractograms of the monohydrate, purified and anhydrous species obtained by the described method.

FIG. 15 gives a comparison between the diffractometry profiles of argatroban anhydrous, argatroban monohydrate and purified argatroban. As is evident from the superimposition, the three crystalline structures are clearly different.

The examples given below for the purposes of non limiting illustration of the synthesis process of the invention, relate to the different steps that form the method in its entirety and refer to the previously reported scheme.

Experimental Part

Examples of the Synthesis of Purified Argatroban (IV) from (2R,4R)-1-[N$^G$-nitro-N$^2$-(3-methyl-8-quinolinesulphonyl)-L-arginyl]-4-methyl-2-piperidine carboxylic acid (II)

Example 1

Treatment of Crude Argatroban with NaOH and Separation of the Purified Argatroban with Isopropanol A one-litre glass autoclave was fed with 60 g of (2R,4R)-1-[N$^G$-nitro-N$^2$-(3-methyl-8-quinolinesulphonyl)-L-arginyl]-4-methyl-2-piperidine carboxylic acid, 480 ml of methanol, 120 ml of acetic acid and 20 g of palladium on 5% carbon (60% wetted).

The mixture thus obtained was treated, under vigorous stirring, at 85° C. in a 8.5 bar hydrogen atmosphere for 8.5 hours.

The mass was then cooled to room temperature and the catalyst removed by filtration. The obtained solution was concentrated to a residue under reduced pressure. 600 ml of methylene chloride, 300 ml of water and 75 ml of an aqueous solution of 30% sodium hydroxide were added to the oily residue obtained until the residual acetic acid was neutralized (pH=7.5).

30 ml of methanol were then added and the mixture maintained under agitation for 1 hour. The aqueous phase was removed and the organic phase washed twice with 300 ml of water adding each time the necessary quantity of methanol to achieve a good separation.

The solution in methylene chloride (a third of the total solution) thus obtained was then percolated into a 500 ml jacketed reactor containing 120 ml of 2-propanol. The mass was then heated and 200 ml of solvent were distilled off. The solution was then cooled to 0° C. over a period of 2 hours and maintained at this temperature for 3 hours.

The solid obtained by crystallization was filtered off and dried at 50° C. under vacuum for 16 hours, giving 16.0 g of purified (2R,4R)-4-methyl-1-[$N^2$-[(1,2,3,4-tetrahydro-3-methyl-8-quinolylsulphonyl]-L-arginyl]pipecolic acid (IV). Yield=86%.

Example 2

Treatment of the Crude Argatroban with NaOH and Crystallization from Normal Propanol A one-litre glass autoclave was fed with 50 g of (2R,4R)-1-[$N^G$-nitro-$N^2$-(3-methyl-8-quinolinesulphonyl)-L-arginyl]-4-methyl-2-piperidine carboxylic acid, 375 ml of methanol, 95 ml of acetic acid and 16.4 g of palladium on 5% carbon (60% wetted).

The mixture thus obtained was treated, under vigorous stirring, at 85° C. in a 8.5 bar hydrogen atmosphere for 8 hours.

The mass was then cooled to room temperature and the catalyst removed by filtration. The obtained solution was concentrated to a residue under reduced pressure.

570 ml of methylene chloride was added to the oily residue obtained and the solution divided into two parts. Half of the obtained solution was fed into a jacketed 1-litre glass reactor and to it 120 ml of water were added. The acetic acid residue was then neutralized by addition of a 30% sodium hydroxide solution until pH=7.5 was achieved. In order to obtain a net separation between the organic phase and aqueous phase 12 ml of methanol were then added. The mixture was maintained under stirring for 1 hour, then the aqueous phase was removed and the organic phase washed twice with 120 ml of water, adding each time the necessary quantity of methanol to achieve a good separation.

The solution in methylene chloride thus obtained was then percolated into a 500 ml jacketed reactor containing 140 ml of 1-propanol. The mass was then heated to 55° C. to distill off the dichloromethane present. The solution was then cooled to 0° C. over a period of 2 hours and maintained at this temperature for 2 hours.

The solid obtained by crystallization was filtered off and dried at 50° C. under vacuum for 16 hours, giving 17.0 g of purified (2R,4R)-4-methyl-1-[$N^2$-[(1,2,3,4-tetrahydro-3-methyl-8-quinolylsulphonyl]-L-arginyl]pipecolic acid (IV). Yield=73%.

Example 3

Treatment of Crude Argatroban without Neutralization and with Crystallization from Isopropanol Half of the compound (III) solution in dichloromethane obtained in example 2 was extracted twice with a mixture of 120 ml of water and 12 ml of methanol. The solution in methylene chloride thus obtained was then percolated into a 500 ml jacketed reactor containing 140 ml of 2-propanol, the mass obtained was concentrated by distillation.

When the distillation was complete the temperature was brought to 90° C., the mass left under agitation for 1 hour, cooled to 20° C. and finally to 0° C. where it was maintained for 2 hours.

The solid obtained by crystallization was filtered off and dried at 50° C. under vacuum for 16 hours to give 21.5 g of purified (2R,4R)-4-methyl-1-[$N^2$-[(1,2,3,4-tetrahydro-3-methyl-8-quinolylsulphonyl]-L-arginyl]pipecolic acid (IV). Yield=93%.

Examples of Argatroban Monohydrate (I) Synthesis from (2R,4R)-1-[$N^G$-nitro-$N^2$-(3-methyl-8-quinolinesulphonyl)-L-arginyl]-4-methyl-2-piperidine carboxylic acid (II)

Example 4

Treatment of Crude Argatroban with $NH_3$ to Directly Obtain the Monohydrate Form A 250 ml glass autoclave was fed with 20 g of (2R,4R)-1-[$N^G$-nitro-$N^2$-(3-methyl-8-quinolinesulphonyl)-L-arginyl]-4-methyl-2-piperidine carboxylic acid (II), 160 ml of methanol, 10.4 ml of acetic acid and 5.6 g of palladium on 5% carbon (50% wetted).

The mixture thus obtained was treated, under vigorous stirring, at 85° C. in a 9 bar hydrogen atmosphere for 8 hours.

The mass was then cooled to room temperature and the catalyst removed by filtration. The obtained solution was concentrated at atmospheric pressure.

After having distilled 60 ml of solvent, the solution was cooled to 0° C. and neutralized with 12 ml of an aqueous solution of 30% ammonia.

Excess ammonia was removed under vacuum, then 700 ml of water were added to the reaction mixture. The solution obtained was heated at reflux (at about 95° C.), maintained under stirring at this temperature for 1 hour, then cooled to 20° C. over a period of 4 hours and maintained at this temperature for 8 hours.

The crystalline precipitate was filtered off and dried at 80° C. at atmospheric pressure and nitrogen flow for 8 hours to give 15.8 g of argatroban monohydrate (I) (HPLC purity=99.8%; isomer ratio=63.8:36.2; KF=3.5%). Yield=82.4%.

Example of Crystallization for Obtaining Argatroban Monohydrate (I) from Purified Argatroban (IV)

Example 5

Crystallization with 35 Volumes of Water and 5.5 Volumes of Methanol

A jacketed steel reactor was fed with 2218 g of purified (2R,4R)-4-methyl-1-[$N^2$-[(1,2,3,4-tetrahydro-3-methyl-8- quinolylsulphonyl]-L-arginyl]pipecolic acid (IV), 12192 ml of methanol and 77647 ml of demineralized water. The mixture obtained, to which were added 66.6 g of decolorizing carbon, was heated at reflux and maintained at this temperature for 1 hour under nitrogen. The carbon was then removed under hot conditions by filtration.

The solution was then brought to reflux and maintained at this temperature for 2 hours, cooled to the temperature of initial crystallization (75° C.) over a period of 1 hour, maintained at this temperature for 1 hour, then cooled to 20° C. over 4.5 hours and left under stirring for 6 hours.

The solid obtained by crystallization was filtered off, washed with 2218 ml of demineralized water and dried at 55° C. under reduced pressure for 12 hours to give 1998 g of (2R,4R)-4-methyl-1-[$N^2$-[(1,2,3,4-tetrahydro-3-methyl-8-quinolylsulphonyl]-L-arginyl]pipecolic acid (I) monohydrate. (HPLC purity=99.9%; isomer ratio=63.2:36.8; KF=3.5%). Yield=87%.

Example of Crystallization to Obtain Argatroban Anhydrous (V)

Example 6

Crystallization from Water

A jacketed glass reactor was fed with 100 ml of water and brought to 80° C.; 0.8 g of argatroban monohydrate was added at this temperature. The mass was maintained under stirring for 10 minutes at this temperature then the un-dissolved residue was removed by filtration. The mother liquors were quickly cooled to 15° C. (in about 2 minutes) and maintained at this temperature for 1 hour. The obtained solid was separated by filtration and dried at 80° C. at atmospheric pressure for 10 hours in a nitrogen flow, giving 0.5 g of argatroban anhydrous (HPLC purity=99.9%; isomer ratio=60.6:39.4; KF=0.26%). Yield 65%.

The invention claimed is:

1. A method for preparing argatroban monohydrate comprising at least the steps of:
    concentrating a reaction mass containing crude argatroban to a stirrable residue;
    dissolving the residue containing crude argatroban with an organic solvent and separating a purified argatroban by crystallization by treating the organic solution with a crystallization medium solvent selected from isopropanol and normal-propanol;
    separating argatroban monohydrate by re-crystallizing the purified argatroban isolated in the preceding step from a methanol and water mixture solution by adding a decolorizing carbon, heating at the reflux temperature followed by carbon filtering and to controlled cooling from the reflux temperature to a temperature between 15 and 25° C. in a time between 11-17 hours.

2. A method for preparing argatroban anhydrous comprising at least the steps of:
    preparing argatroban monohydrate according to a method as defined in claim 1;
    re-crystallizing thereof after dissolution in water by quickly cooling to a temperature of 10-20° C. in a time not greater than 2 minutes.

3. Argatroban anhydrous characterized by having:
    melting point of 220° C. with decomposition;
    I.R. spectrum (KBr) (cm$^{-1}$) of 3432, 1265, 1164;
    differential scanning calorimetry with an endothermic event at about 215° C.;
    XRPD: Peak No. 1 Angle (2θ) 7.790, Relative intensity (%) 64; Peak No. 2 Angle (2θ) 9.560, Relative intensity (%) 95; Peak No. 3 Angle (2θ) 10.480, Relative intensity (%) 27; Peak No. 4 Angle (2θ) 11.320, Relative intensity (%) 75; Peak No. 5 Angle (2θ) 12.120, Relative intensity (%) 61; Peak No. 6 Angle (2θ) 14.640, Relative intensity (%) 23; Peak No. 7 Angle (2θ) 16.010, Relative intensity (%) 25; Peak No. 8 Angle (2θ) 16.940, Relative intensity (%) 14; Peak No. 9 Angle (2θ) 18.030, Relative intensity (%) 45; Peak No. 10 Angle (2θ) 18.900, Relative intensity (%) 100; Peak No. 11 Angle (2θ) 20.960, Relative intensity (%) 47; Peak No. 12 Angle (2θ) 22.550, Relative intensity (%) 53; Peak No. 13 Angle (2θ) 24.370, Relative intensity (%) 61; Peak No. 14 Angle (2θ) 26.170, Relative intensity (%) 81; Peak No. 15 Angle (2θ) 28.300, Relative intensity (%) 32; Peak No. 16 Angle (2θ) 30.960, Relative intensity (%) 40; Peak No. 17 Angle (2θ) 33.970, Relative intensity (%) 40; Peak No. 18 Angle (2θ) 38.930, Relative intensity (%) 23.

4. Purified argatroban characterized by having:
    melting point of 183-185° C.;
    I.R. spectrum (KBr) (cm$^{-1}$) of 3399, 1270, 1160;
    differential scanning calorimetry with an endothermic event at about 160° C.;
    XRPD: Peak No. 1 Angle (2θ) 6.800, Relative intensity (%) 100; Peak No. 2 Angle (2θ) 7.840, Relative intensity (%) 12; Peak No. 3 Angle (2θ) 9.800, Relative intensity (%) 13; Peak No. 4 Angle (2θ) 10.020, Relative intensity (%) 13; Peak No. 5 Angle (2θ) 10.700, Relative intensity (%) 6; Peak No. 6 Angle (2θ) 11.780, Relative intensity (%) 5; Peak No. 7 Angle (2θ) 13.080, Relative intensity (%) 12; Peak No. 8 Angle (2θ) 13.540, Relative intensity (%) 32; Peak No. 9 Angle (2θ) 14.540, Relative intensity (%) 21; Peak No. 10 Angle (2θ) 16.900, Relative intensity (%) 8; Peak No. 11 Angle (2θ) 17.540, Relative intensity (%) 18; Peak No. 12 Angle (2θ) 18.640, Relative intensity (%) 14; Peak No. 13 Angle (2θ) 19.060, Relative intensity (%) 13; Peak No. 14 Angle (2θ) 19.620, Relative intensity (%) 13; Peak No. 15 Angle (2θ) 20.000, Relative intensity (%) 20; Peak No. 16 Angle (2θ) 21.420, Relative intensity (%) 16; Peak No. 17 Angle (2θ) 21.780, Relative intensity (%) 21; Peak No. 18 Angle (2θ) 22.660, Relative intensity (%) 15; Peak No. 19 Angle (2θ) 23.680, Relative intensity (%) 15; Peak No. 20 Angle (2θ) 24.080, Relative intensity (%) 16; Peak No. 21 Angle (2θ) 24.740, Relative intensity (%) 25; Peak No. 22 Angle (2θ) 25.340, Relative intensity (%) 9; Peak No. 23 Angle (2θ) 26.480, Relative intensity (%) 10; Peak No. 24 Angle (2θ) 27.580, Relative intensity (%) 10; Peak No. 25 Angle (2θ) 28.220, Relative intensity (%) 7; Peak No. 26 Angle (2θ) 29.120, Relative intensity (%) 8; Peak No. 27 Angle (2θ) 29.740, Relative intensity (%) 11; Peak No. 28 Angle (2θ) 31.820, Relative intensity (%) 9; Peak No. 29 Angle (2θ) 34.840, Relative intensity (%) 7; Peak No. 30 Angle (2θ) 40.580, Relative intensity (%) 6; and by being solvated with isopropanol.

5. The method for preparing argatroban monohydrate according to claim 1, further comprising the step of:
    preparing the crude argatroban from (2R,4R)-1-[$N^G$-nitro-$N^2$-(3-methyl-8-quinolinesulphonyl)-L-arginyl]-4-methyl-2-piperidine carboxylic acid in methanol/acetic acid.

6. The method for preparing argatroban monohydrate according to claim 1, wherein the reaction mass is treated with an aqueous solution of a base to bring the pH of the mixture itself to between 7.0 and 7.5.

7. The method for preparing argatroban monohydrate according to claim 6, wherein the base solution is selected from sodium hydroxide, sodium bicarbonate and ammonia at a concentration comprised between 10 and 30%.

8. The method for preparing argatroban monohydrate according to claim 1, wherein the crystallization or re-crystallization from methanol and water is achieved by subjecting the mass to the following temperature gradient: heating to 90-95° C., maintenance at reflux temperature for a time between 1 and 3 hours, cooling to 70-75° C. in at least one hour and maintenance at this temperature for at least one hour, cooling to 20° C. in a time comprised between 2 and 6 hours and maintenance at this temperature for at least 6 hours.

9. The method according to claim 8, wherein the methyl alcohol and water mixture medium solvent has a concentration of between 10 and 20% of alcohol and is in a quantity up to 50 volumes per gram of crude or purified argatroban.

10. The method for preparing argatroban monohydrate according to claim 1 further comprising the step of drying the obtained crystalline precipitate consisting of argatroban monohydrate.

11. The method for preparing argatroban monohydrate according to claim 1, wherein the crystallization of purified argatroban is from medium solvent consisting of isopropanol.

* * * * *